United States Patent
Asmussen et al.

(10) Patent No.: US 6,599,511 B1
(45) Date of Patent: *Jul. 29, 2003

(54) PHARMACEUTICAL COMPOSITION CONTAINING DESOXYPEGANINE FOR THE TREATMENT OF DRUG DEPENDENCE

(75) Inventors: Bodo Asmussen, Bendorf (DE); Thomas Hille, Neuwied (DE); Hans-Rainer Hoffmann, Neuwied (DE); Klaus Opitz, Münster (DE)

(73) Assignees: LTS Lohmann Therapie-Systeme AG, Andernach (DE); HF Aezneimittelforschung GmbH, Werne (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/889,648

(22) PCT Filed: Feb. 8, 2000

(86) PCT No.: PCT/EP00/00974

§ 371 (c)(1),
(2), (4) Date: Oct. 17, 2001

(87) PCT Pub. No.: WO00/48582

PCT Pub. Date: Aug. 24, 2000

(30) Foreign Application Priority Data

Feb. 19, 1999 (DE) .......................................... 199 06 978

(51) Int. Cl.⁷ .............................. A61K 9/00; A61K 9/70; A61K 9/48; A61K 9/52; A61K 9/20; A61K 9/22; A01N 43/42; A01N 43/58; A01N 43/40; A01N 43/36

(52) U.S. Cl. ........................ 424/400; 424/451; 424/457; 424/464; 424/468; 424/725; 424/776; 424/449; 514/290; 514/291; 514/292; 514/250; 514/349; 514/408; 514/631

(58) Field of Search .................................. 424/400, 464, 424/725, 776, 449, 451, 457, 468; 514/810, 811, 812, 813, 964, 290, 291, 292, 250, 349, 408–631

(56) References Cited

U.S. PATENT DOCUMENTS 5,591,738 A * 1/1997 Lotsof ......................... 514/214
5,643,905 A * 7/1997 Moormann .................. 514/215

OTHER PUBLICATIONS

Database WPI Section Ch, Week 197913 Derwent Publications Ltd., London, GB; AN 1979–25213B (XP002151986).
Tulyaganov, et al, "The pharmacological characteristics of deoxypeganine hydrochloride," Farmakol. Toksikol. (Moscow) (1986), 49(3), pp. 37–40 (XP000957689).
Muratova, et al, "Toxicology of the new pharmaceutical preparation of dehydrooxypeganine hydrochloride" Med. Zh. Uzb. 1984, (1), 53–5 (XP000957819) (abstract).
Vovin et al, Zh Nevropatol Psikhiatr Im S S Korsakova, 1991; 91 (2): 111–5.*

* cited by examiner

*Primary Examiner*—Michael G. Hartley
*Assistant Examiner*—Sharmila S. Gollamudi
(74) *Attorney, Agent, or Firm*—Frommer Lawrence & Haug LLP

(57) ABSTRACT

Desoxypeganine and its pharmaceutically acceptable acid addition salts can be used in the treatment of drug addiction or drug dependence. Said substances are administered preferably in a continuos and controlled manner. The pharmaceutical administration form enables controlled release, e.g. for oral transdermal or another route of parenteral administration.

10 Claims, No Drawings

PHARMACEUTICAL COMPOSITION CONTAINING DESOXYPEGANINE FOR THE TREATMENT OF DRUG DEPENDENCE

Desoxypeganine and/or its pharmaceutically acceptable acid addition salts can be used for the treatment of drug dependence. These substances are administered in a controlled manner, preferably in a continuous manner. The pharmaceutical administration form makes controlled release possible for, for example, oral, transdermal or alternatively parenteral administration.

The invention relates to the use of desoxypeganine and its pharmaceutically suitable acid addition salts for the treatment of drug dependence and/or drug addiction. These compounds are released, for example, continuously or otherwise in a controlled manner from appropriate pharmaceutical formulations, which are administered, for example, orally, transdermally or otherwise parenterally. Such administration forms can also make subcutaneous, sublingual or intramuscular administration possible. Finally, administration as an implant is also possible. The term parenteral, however, also comprises other administration forms apart from the oral form, i.e., for example, also rectal, intravenous, intramuscular, intraperitoneal and nasal administration.

Desoxypeganine or a pharmaceutically acceptable acid addition salt or a mixture of base and salt is used for the substitution therapy of drug addicts such as, for example, opiate addicts, for example heroin addicts or cocaine addicts.

Desoxypeganine has in fact been investigated in detail in the former Soviet Union and its pharmacological actions have been intensively researched; the use according to the invention of a desoxypeganine-containing formulation for the treatment of drug addiction and/or drug dependence, however, has not been described until now.

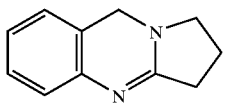

Desoxypeganine (1,2,3,9-tetrahydropyrrolo[2,1-b] quinazoline) is an alkaloid of the empirical formula $C_{11}H_{12}N_2$ having the above structure, which is contained in plaints from the family Zygophyllaceae. It is commercially obtainable as an acid addition salt (hydrochloride).

On account of its pharmacological properties, desoxypeganine belongs to the group of reversibly acting cholinesterase inhibitor, is closely related in its actions to physostigmine and neostigmine, but is distinguished by particular specific properties. Desoxypeganine in fact inhibits not only acetylcholinesterase, but also monoamine oxidase. This advantage offsets its somewhat lower cholinesterase inhibitory action based on the unit of weight (in comparison with physostigmine).

In contrast to neostigmine, desoxypeganine crosses the blood-brain barrier and antagonizes the cerebral actions of cholonergic toxins. Desoxypeganine is obtained by isolation from the harmel peganum (Peganum harmala) or by synthesis.

Pharmaceutical forms which release the active compounds in a controlled manner are already known in the prior art. The administration of pharmaceutically active compounds by means of such formulations can be carried out orally, transdermally or otherwise parenterally. In medicaments of this type, the desoxypeganine can be present as such or in the form of pharmaceutically acceptable acid addition salts, e.g. as the hydrohalide, in particular hydrochloride or hydrobromide, or as a salt of another pharmaceutically acceptable acid, e.g. as a citrate, tartrate or acetate. These agents furthermore contain, as a rule, excipients, such as vehicles, flow-improving agents, solvents and oils, whose nature and amount varies depending on the presentation form. In general, the content of active compound in the medicament, calculated as free desoxypeganine, is between 0.1 and 50% by weight, preferably 2 and 15% by weight.

The active compound or the active compound mixture is released by the corresponding pharmaceutical formulation over a relatively long period, e.g. for approximately 12, 16, 24, or 72 hours. In special administration forms, the period of active compound release can also extend over more than 3 days.

In principle, transdermal administration of desoxypeganine and its pharmaceutically acceptable acid addition salts is to be preferred to oral or parenteral administration. It is clear that a transdermal therapeutic system (TTS) offers greatly increased safety with respect to improper administration. Thus extraction of the -active compound from the TTS matrix without expert knowledge is not possible. Thus improper parenteral administration by an addict to satisfy his/her addiction represents a significantly lower risk than would be presented, for example, in the case of a solution to be administered orally. Therapy with the aid of a transdernial therapeutic system can be carried out without direct supervision or without the physician. A further advantage is the direct control of the dose delivered by means of the release area. In the case of withdrawal therapy, the necessary doses can be tailored simply to the respective needs of the addict. In addition, the known advantages of transdermal administration are provided, namely:

avoidance of the high pharmaceutical dose necessary in the case of oral administration, which has to take account of the first-pass effect, and more controllable blood levels.

The object on which the invention is based has now been achieved by a transdermal therapeutic systems (TTS) for the administration of desoxypeganine and/or one of its pharmaceutically acceptable acid addition salts as an active compound for the treatment of drug dependence or drug addiction, having a self-adhesive stratiforin matrix containing active compound(s), where in or on one side of the matrix a covering film (backing liner) and in or on the other side of the matrix a removable film (release liner) are provided.

If appropriate, the object on which the invention is based can also be used by a transdermal therapeutic systems (TTS) for the administration of desoxypeganine and/or one of its pharmaceutically tolerable salts as an active compound for the treatment of drug dependence and/or drug addiction, having an outer covering layer, a reservoir for the active compound, an adhesive element for the skin contact of the patch and a removable protective layer, the reservoir optionally containing permeation promoters, stabilizers, emulsifiers, thickening agents and/or other customary excipients in addition to the active compound.

The transdermal therapeutic system according to the invention can comprise 0.1 to 50% by weight of desoxypeganine, based on the matrix or the reservoir of the patch which can be applied. A content of 5 to 20% by weight of desoxypeganine is particularly preferred.

The covering film of the transdermal therapeutic system according to the invention can consist of polyester, polypropylene, polyethylene or polyurethane, in each case optionally metalized, and the removable film of polyester, polypropylene or coated paper.

Pressure contact adhesives or hot-melt contact adhesives based on polyacrylate, polyisobutylene, silicone, styrene/butadiene copolymer or styrene/isoprene copolymer are suitable for the matrix of a transdermal therapeutic system according to the invention.

The transdermal therapeutic system according to the invention can comprise a semipermeable membrane, in particular a membrane controlling the rate of active compound release. The membrane can be provided based on silicone, polypropylene, ethylene/vinyl acetate or polyvinyl acetate.

In the transdermal therapeutic system according to the invention, the adhesive element can be provided in the form of a layer covering the reservoir (if no membrane is provided) or in the form of a layer covering the membrane completely or only annularly on its periphery. A pressure-sensitive adhesive based on silicone or acrylate can be used for the adhesive element.

By means of the administration of desoxypeganine and its pharmaceutically suitable acid addition salts or a mixture of base and salt, the symptoms of drug dependence and/or drug addiction, in particular the physical withdrawal symptoms, but also the psychological withdrawal symptoms, are decreased or eliminated.

The procedure for the treatment of the psychological and/or physical withdrawal symptoms of drug addiction and/or drug dependence comprises the administration of an efficacious amount of desoxypeganine and/or a pharmaceutically acceptable salt of desoxypeganine to a person who is suffering from said withdrawal symptoms. Preferably, in this procedure the active compound is used in the form of an administration form having delayed release of this active compound or active compound mixture.

The invention relates to the use of desoxypeganine and/or a pharmaceutically acceptable salt of desoxypeganine for the production of an administration form (medicament) having delayed release of this active compound or active compound mixture for the treatment of the psychological and/or physical withdrawal symptoms of drug addiction and/or drug dependence.

What is claimed is:

1. A method for the treatment of drug addiction and/or drug dependence in a patient, who is addicted to drugs or is dependent on drugs, which comprise administering a pharmaceutical formulation comprising desoxypeganine and/or a pharmaceutically acceptable salt of desoxypeganine in a controlled and continuous manner to said patient.

2. The method according to claim 1, wherein the pharmaceutical formulation is administered orally or transdermally.

3. The method according to claim 1, wherein the pharmaceutical formulation is administered parenterally.

4. The method according to claim 1, wherein the pharmaceutical formulation releases desoxypeganine and/or a pharmaceutically acceptable salt of desoxypeganine over a time period of between 12 hours to 72 hours.

5. The method according to claim 4, wherein the pharmaceutical formulation is a transdermal therapeutic system comprising a cover layer, a reservoir, which contains desoxypeganine and/or a pharmaceutically acceptable salt of desoxypeganine and an adhesive element.

6. A pharmaceutical preparation, which comprises, as an active compound, desoxypeganine and/or a pharmaceutically acceptable salt of desoxypeganine and releases desoxypeganine and/or a pharmaceutically acceptable salt of desoxypeganine in a controlled manner, wherein the amount of desoxypeganine and/or a pharmaceutically acceptable salt present or in said preparation is from 0.1 to 50% by weight of the preparation, calculated as free desoxypeganine.

7. The pharmaceutical preparation according to claim 6, wherein the active compound is released over a period between 12 and 72 hours.

8. The pharmaceutical preparation according to claim 6, which is an oral or transdermal preparation.

9. The pharmaceutical preparation according to claim 6, which is a parenteral preparation.

10. The pharmaceutical preparation according to claim 6, wherein said preparation is a transdermal therapeutic system comprising a cover layer, a reservoir containing desoxypeganine and/or its pharmaceutically acceptable salt and an adhesive element.

* * * * *